United States Patent [19]

Lidert

[11] Patent Number: 4,943,434
[45] Date of Patent: Jul. 24, 1990

[54] INSECTICIDAL HYDROGENATED NEEM EXTRACTS

[75] Inventor: Zev Lidert, Doylestown, Pa.

[73] Assignee: Rohm and Haas Company, Philadelphia, Pa.

[21] Appl. No.: 240,790

[22] Filed: Sep. 2, 1988

Related U.S. Application Data

[63] Continuation-in-part of Ser. No. 106,755, Oct. 6, 1987, abandoned.

[51] Int. Cl.$^5$ .............................................. A01N 65/00
[52] U.S. Cl. ................................ 424/195.1; 514/453; 424/405
[58] Field of Search ...................... 424/195.1; 514/453

[56] References Cited

U.S. PATENT DOCUMENTS 4,556,562 12/1985 Larsen ............................... 424/195.1

FOREIGN PATENT DOCUMENTS 3420230 1/1986 Fed. Rep. of Germany .

OTHER PUBLICATIONS

Chem. and Engineering News, May 27, 1985, pp. 46–51.
Warthen et al., U.S. Dep. Agric., Agric. Rev. Man. ARM-NE-4.
Butterworth et al., J. Insect Physiol., 17: 969–977 (1971).
Butterworth et al., J. Chem. Soc. Perkin Tran. I, 2445-2450 (1972).
Morgan, Proc. 1st Int. Neem Conf., Rottach-Egern, 43–52 (1980).
Broughton et al., Chem. Commun. 46 (1986).
Rombold et al., Abstracts of the Third International Neem Conf., Nairobi, Kenya (1986).
Yamasaki et al., J. Agric. Food Chem., 35, 467–471 (1987).
4017626 WPI Acc. No.: 86-021017/04.
3786154 WPI Acc. No.: 85-113075/19.
3769718 WPI Acc. No.: 85-096639/16.
3768415 WPI Acc. No.: 85-095336/16.
3768414 WPI Acc. No.: 85-095335/16.
2968252 WPI Acc. No.: 82-16212E/09.
2968250 WPI Acc. No.: 82-1621E/09.
1646392 WPI Acc. No.: 79-06439B/04.
357682 WPI Acc. No.: 72-18328T/12.
Jacobsen, Proc. id. Int. Neem Conf., Rottach-Egern 1980, pp. 33–42.
Jacobsen et al., Proc. 2nd Int. Neem Conf. Ranischolzhausen 1983, pp. 31–42.
Feuerhake et al., Journal of Plant Diseases and Protection 42(6), 643–649, 1985.

Primary Examiner—Ferris H. Lander
Attorney, Agent, or Firm—Barbara V. Maurer

[57] ABSTRACT

This invention relates to insecticidal hydrogenated extracts of seeds of the neem tree (*Azadirachta indica*), compositions containing the extracts and methods of their use.

29 Claims, 2 Drawing Sheets

INSECTICIDAL HYDROGENATED NEEM EXTRACTS

This application is a continuation-in-part application of U.S. Ser. No. 106,755 filed Oct. 6, 1987 now abandoned.

This invention relates to extracts of the seeds of the neem tree (*Azadirachta indica*) which are hydrogenated to provide materials useful as insecticides, compositions containing those and methods of their use.

BACKGROUND OF THE INVENTION

The search for compositions which have a combination of excellent insecticidal activity and desirable low toxicity to plants and mammals is a continuing one because of factors such as the desire for compounds exhibiting greater insecticidal activity, better selectivity, low environmental impact, low production cost and effectiveness against insects resistant to many known insecticides.

The hydrogenated materials of the present invention are particularly suitable for controlling plant destructive insects in crops of cultivated plants, ornaments and forestry.

Various parts of the neem (or nim) tree, *Azadirachta indica* have long been used in India for their reputed medicinal or insecticidal properties. This subtropical tree is native to the arid regions of India, Pakistan, Sri Lanka, and parts of Southeast Asia and Africa.

Although all parts of the neem tree appear to have natural resistance to pests and diseases, the seeds appear to have the greatest resistance. Formulations and extracts of the seeds have been shown to be effective against many species of crop pests, including gypsy moths, Japanese beetles, aphids, tobacco budworms and boll weevils See for example, *Chem. and Engineering News*, May 27, 1985, pp 46-51 and Warthen et al., *U.S. Dep. Agric., Agric. Rev. Man.*, ARM-NE-4. Neem seed extract is considered to be a broad-spectrum insecticide.

Several active compounds have been identified in the seeds.

In *J. Insect Physiol.*, 17: 969-977 (1971) an investigation of the locust feeding inhibition of the seeds of the neem tree, *Azadirachta Indica* A. Juss and the isolation of a major constituent, azadirachtin, is disclosed. No chemical derivatives of azadirachtin are disclosed.

In *J. Chem. Soc. Perkin Trans. I*, 2445-2450 (1972) a proposed structure of azadirachtin and its functional groups is disclosed. The preparation of dihydroazadirachtin and a non-reproducible preparation of tetrahydroazadirachtin are also disclosed. No biological activity for the derivatives of azadirachtin is disclosed.

In *Proc. 1st Int. Neem Conf.*, Rottach-Egern, 43-52 (1980) certain biological properties of azadirachtin and some of its derivatives are disclosed. Hydrogenation of the double bond of the dihydrofuran ring is disclosed to have little or no effect on the biological activity of azadirachtin. Removal of the acetyl group is also to have little or no effect on the biological activity.

In *Chem. Commun.*, 46 (1986) the structures of azadirachtin, dihydroazadirachtin and tetrahydroazadirachtin are disclosed. No biological activity is disclosed for those compounds.

In abstracts of the 3rd Int. Neem Conference, Nairobi, Kenya, 1986, the biological activity of azadirachtins including dihydrogenated chemical derivatives of azadirachtin A and azadirachtin B is disclosed.

In DE 3420 230A a new steroid azadirachtin, isolated from *Azadirachta Indica* and used as an insecticide, nematicide, disinfectant, fertilizer, antiinflammatory, antiulcer agent and cold agent, is disclosed.

In *J. Agric. Food Chem.*, 35, 467-471 (1987) eight derivatives of azadirachtin and their growth inhibitory and lethal activities against *Heliothis* Virescens are disclosed. None of the derivatives had enhanced activity over azadirachtin.

While azadirachtin has been shown to be active as an insecticide, it has not come into commercial use because it is a highly complex compound which is difficult and expensive to isolate in a pure state.

Crude or partially purified extracts of the neem seed have been found to be effective insecticides in the form of liquid and powdered compositions.

In U.S. Pat. No. 4,556,562, an aqueous storage-stable neem seed extract composition is disclosed and claimed. The patent teaches that adjustment of the pH of the composition to the range of 3.5 to 6.0 is necessary to provide for a stable aqueous composition of the extract.

Notwithstanding the above advances there remains a need for an economical, stable composition effective to control pests.

SUMMARY OF THE INVENTION

It has now been discovered that hydrogenation of extracts of neem seeds provides materials which have greater insecticidal activity than extracts which have not been hydrogenated. This greater activity is unexpected in view of the fact that the activity of pure dihydroazadirachtin is disclosed to be the same or less than that of pure azadirachtin.

BRIEF DESCRIPTION OF THE DRAWINGS

The following HPLC curves are presented in the drawings.

DESCRIPTION OF THE PREFERRED EMBODIMENTS

Figure 1:
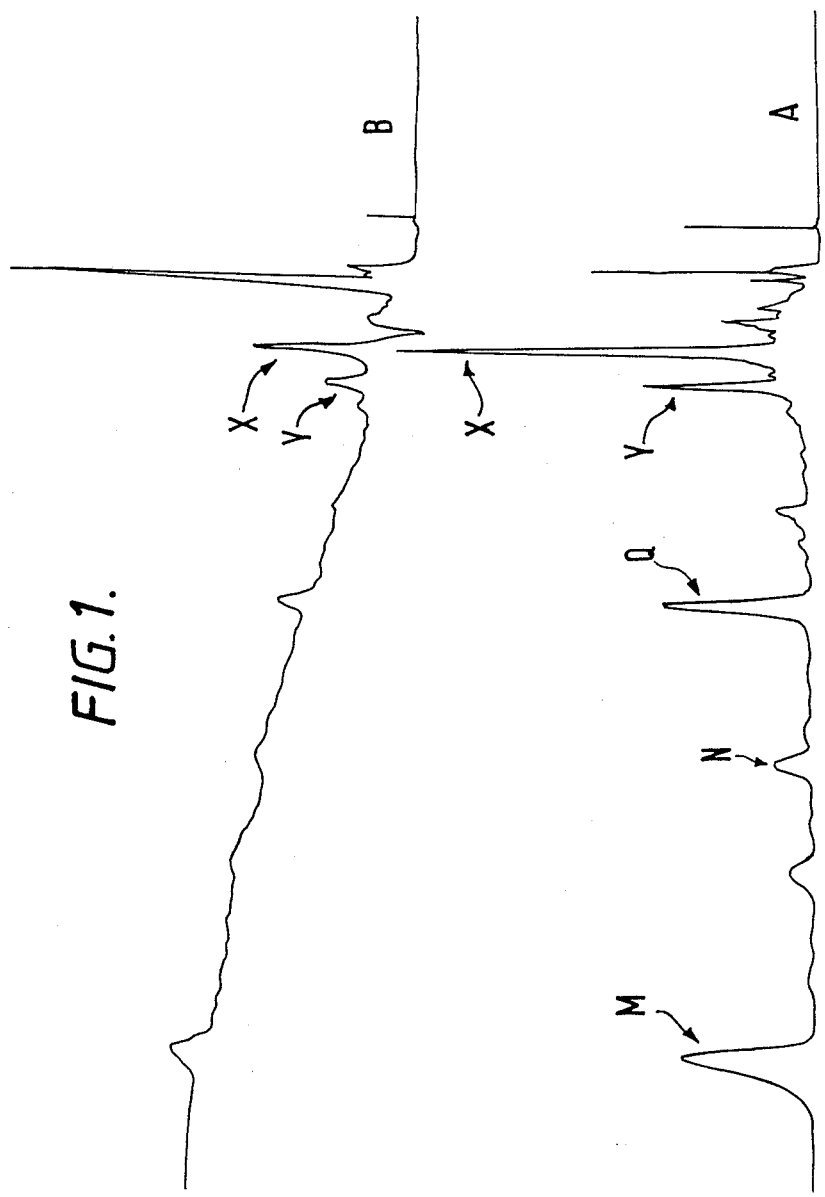
FIG. 1 shows the uv absorption (A) and refractive index (B) for a non-hydrogenated neem seed extract.

In accordance with the instant invention, there is provided a new insecticidal material from the neem seed obtained by the hydrogenation of neem seed extract. The hydrogenated material of the instant invention comprises dihydroazadirachtin and/or tetrahydroazadirachtin and hydrogenated derivatives of other compounds contained in the extract.

The hydrogenated material of the invention has greater insecticidal activity and longer residual activity than the non-hydrogenated extract.

In general, the hydrogenated material of the invention is obtained by first preparing an extract of neem seeds according to known methods so as to obtain a crude or partially purified extract. The extract is then hydrogenated to obtain the desired product.

More particularly, the neem seed or neem seed kernel is first ground to a particle size of between about 0.1 and 10 mm in diameter. The particles are then extracted with a polar solvent to obtain a neem seed extract. The neem seed extract is then hydrogenated to obtain the insecticidal neem seed material of the invention.

In a preferred embodiment of the invention the neem seed extract to be hydrogenated contains azadirachtin and tigloyl-azadirachtol as well as a number of unidentified other compounds. Two isomers of tigloyl-azadirachtol have been reported in the literature, the 1-tigloyl and 3-tigloyl isomers (Kubo, et al., *Tetrahedron Letters*, 25, 4729-4732 (1986); Klenk et al., *Chem Commun.* 523 (1986); Bilton et al., *Tetrahedron*, 43 2805, 1815 (1987). The extracts of the instant invention can contain one or the other or both of the isomers. Other compounds which may be in the extract include but are not limited to salinin, nimbin, 3-acetoxy-7-tigloyl vilasinin lactone, 17-epiazadiradion, 17-beta-hydroxy azadiradion, 1-alpha-methoxy-1,2-dihydroepoxyazadiradion, diepoxyazadiradion, the benzoate esters derived from azadiradion, epoxyazadiradion and gedunin, diacetylvilasinin, desacetylsalannin, salannol, nimbandiol, 22,23-dihydroxy-220-beta-methoxyazadirachtin, and deacetylazadirachtinol.

When the extract is hydrogenated, dihydroazadirachtin is obtained along with the other compounds in the extract, some or all of which may also have been hydrogenated.

It has been found that it is also possible to partially purify the extract before the hydrogenation step is undertaken. Accordingly, in a more preferred embodiment of the invention, the neem seeds are ground, and then fatty acids and oils are removed, for example by pressing the ground seeds or by extraction with a nonpolar organic solvent. The active compounds are then extracted from the ground seeds with a polar solvent. Water soluble sugars and proteins are removed from the extract and the residue is hydrogenated to obtain the hydrogenated mixture of the invention.

Suitable solvents to remove the fatty acids and oils include, but are not limited to, aliphatic and aromatic hydrocarbons and such other solvents that are known by those skilled in the art, for example hexane, heptane, pentane, petroleum ether, benzene, toluene cyclohexane and xylene. Preferred solvents are the aliphatic hydrocarbons. The most preferred solvents are petroleum ether, hexane and heptane.

Suitable solvents to remove azadirachtin and other compounds from the neem seed include, but are not limited to water, alcohols such as methanol, ethanol, propanol, butyl alcohol, and other solvents such as ethyl acetate, acetonitrile, methyl isobutyl ketone, acetone, methyl t-butyl ether, glyme, dimethylsulfoxide, tetramethylene sulfone, dimethylformamide, chloroform, methylenechloride, carbon disulfide, super critical carbon dioxide, acetic acid and the like and mixtures thereof. Preferred solvents are the aliphatic alcohols. The most preferred solvents are ethanol and methanol and aqueous mixtures thereof.

The water soluble sugars and proteins are removed from the residue by means known to those skilled in the art. In a preferred method, the residue is partitioned between water and a water immiscible polar organic solvent such as ethyl acetate, ethyl acetoacetate, butyl acetate, toluene, diisopropyl ether and 2-pentanone. The most preferred solvent is ethyl acetate.

In an alternative embodiment, the neem seeds are first extracted with a polar solvent such as is disclosed above. The residue is then extracted with a non-polar solvent such as disclosed above to remove the fatty acids and oils from the extract. In a preferred embodiment, neem seed extract obtained in this manner contains azadirachtin.

In a preferred embodiment, the resulting extract from the neem seed contains from about 5% to about 80% of azadirachtin. In a more preferred embodiment the extract contains from about 15% to about 50% of azadirachtin.

The hydrogenation of the neem seed extract is carried out by means known to one skilled in the art. In a preferred embodiment, catalytic hydrogenation is used.

In the catalytic hydrogenation step the hydrogenation is monitored and continued until all of the azadirachtin in the extract has been reduced to either dihydroazadirachtin or tetrahydroazadirachtin. Typically from about 1.0 to about 5 moles of hydrogen per mole of azadirachtin in the extract are absorbed. In a preferred method from about 1 to about 4 moles of hydrogen are absorbed. The choice of solvent and catalyst is evident to one skilled in the art. Examples of solvents include but are not limited to water, aliphatic alcohols, ketones, esters and amides such as methanol, ethanol, n-propanol, isopropanol, t-butyl alcohol, acetone, methylisobutyl ketone, acetonitrile, ethyl acetate and dimethylformamide. The most preferred solvent is methanol or mixtures of methanol and/or water and/or ethyl acetate. Examples of catalysts include palladium on supports such as carbon, silica and calcium carbonate and other metals such as platinum, rhodium, ruthenium and nickel and the like. Preferred catalysts include palladium on carbon, platinum oxide, nickel boride and Raney nickel.

The hydrogenation reduction is preferably carried out at from between 1 and 60 atmospheres of hydrogen at from 10° C. to 50° C. In one embodiment the reaction is carried out at 2-4 atmospheres and about 20° C. In another embodiment the reduction is carried out at higher pressure.

In a preferred hydrogenation step of the invention, azadirachtin is reduced to dihydroazadirachtin. The resulting hydrogenated neem seed extract contains from about 5 to about 50% by weight of dihydroazadirachtin In a preferred embodiment the hydrogenated extract contains from about 15% to about 50% of dihydroazadirachtin.

Surprisingly the hydrogenated extracts of the invention exhibit improved pesticidal activity as compared to the known pesticidal neem seed extracts. Accordingly, the hydrogenated extract of the present invention represents a genuine enrichment of the art.

It is understood that hydrogenation of any extract containing azadirachtin from any plant source is contemplated within the scope of this invention. The plant source can include any part of the plant, for example the seeds, leaves or bark of those plants which contain azadirachtin. Examples of plants which contain azadirachtin include the neem (*Azadirachta indica*) tree and chinaberry (*Melia azedarach*) trees.

The hydrogenated materials of the instant invention are broad spectrum insecticides active against several classes of insects including but not limited to Lepidoptera such as diamondback moth, imported cabbage worm, cabbage looper, tobacco budworm; Coleoptera such as Colorado potato beetle; Homoptera such as green apple aphid, green peach aphid; and Homoptera such as potato leaf hopper.

For the control of insects in agriculture and horticulture the dosage of the extract is calculated based on the concentration of dihydroazadirachtin in the extract. In general, a dosage corresponding to from about 0.1 gram to about 10 kilograms of the dihydroazadirachtin in the hydrogenated extract per hectare may be used and from about 5 grams to about 200 grams per hectare of the dihydroazadirachtin is preferred. The exact amount of dosage for a given situation can be routinely determined and depends on a variety of factors, for example, the substance used, the kind of pest, the formulation used, the state of the crop infested with the pest and the prevailing weather conditions. The term "insecticidal" as employed in the specification and claims of the application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The hydrogenated extract of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance is mixed with conventional inert agronomically acceptable (i.e., plant compatible and/or pesticidally inert) diluents or extenders such as solid type usable in conventional compositions or formulations as is well known in the art. If desired, adjuvants such as surfactants, stabilizers, antifoam agents and antidrift agents may also be added.

Examples of compositions and formulations according to the invention are those known to one skilled in the art and include aqueous solutions and dispersions, oily solutions and oil dispersions, pastes, dusting powders, wettable powders, emulsifiable concentrates, flowables, granules, baits, invert emulsions, aerosol compositions and fumigating candles.

The compositions and formulations are prepared in a known manner to one skilled in the art, for example by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as carboxymethylcellulose and natural and synthetic polymers in the form of powders, granules or latices, such as gum arabic, polyvinyl alcohol, polyvinyl cellulose, and polyvinyl acetate, can be used in the formulations to improve the adherence of this pesticide. Furthermore, a lubricant such as calcium stearate or magnesium stearate may be added to a wettable powder or to a mixture to be granulated.

The hydrogenated extract of the present invention may be employed alone and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific applications made theref rom, such as solutions, emulsions, suspensions, powders, pastes, and granules which are thus ready for use.

As concerns commercially marketed preparations, these generally contemplate carrier composition mixtures in which the hydrogenated extract is present in an amount substantially between about 0.1% and 99% by weight, and preferably between about 1% and 75% by weight, of the mixture. Carrier composition mixtures suitable for direct application in the field generally contemplate those in which the dihydroazadirachtin or tetrahydroazadiractin present in the extract is used in an amount substantially between about 0.0001% and 5%, preferably between about 0.001% and 3%, by weight of the mixture. Thus the present invention contemplates overall formulations and compositions which comprise mixtures of a conventional dispersible carrier such as (1) a dispersible inert finely divided carrier solid, and/or (2) a dispersible carrier liquid such as an inert organic solvent and/or water, with or without a surface-active effective amount of a carrier vehicle assistant (e.g., a surface-active agent, such as an emulsifying agent and/or a dispersing agent), and an amount of the hydrogenated extract generally between about 0.0001% and about 99% by weight of the composition, preferably between about 0.001% and about 90% by weight of the composition, and more preferably between about 0.01% and about 75% by weight of the composition which is effective to control insects.

The hydrogenated extracts can be applied as sprays by methods commonly employed, such as conventional high-gallonage hydraulic sprays, low gallonage sprays, ultra low volume sprays, airblast spray, aerial sprays, and dusts.

Furthermore, the present invention contemplates methods of selectively killing, combatting or controlling pests, which comprises contacting insects with a correspondingly combative or toxic amount (i.e., an insecticidally effective amount) of the hydrogenated extract of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or an area where a crop is to be grown) the active compound of this invention alone or as a constituent of a composition or formulation.

It will be realized, of course, that the concentration of the particular hydrogenated extract utilized in admixture with the carrier vehicle will depend upon such factors as the type of equipment employed, method of application, area to be treated, types of pests to be controlled and degree of infestation. In addition to the aforementioned ingredients, the preparations according to the invention may also contain other substances commonly used in preparations of this kind.

The following examples are presented to illustrate the invention and are not to be construed as limiting in scope. All parts and percentages are by weight unless otherwise indicated.

EXAMPLE 1

Dehulled neem seeds (1 kg) were ground to about 1 mm diameter particles in a Waring blender. The ground particles were extracted with hexane ($4 \times 1$ liter) and the extract was discarded. The solid residue was extracted with ethanol (4×1 liter). The ethanol extracts were combined and solvent removed to yield 83.5 grams of extract reside. The residue was partitioned between 95% methanol (500 ml) and hexane (500 ml), the hexane layer was separated and discarded and the solvent was removed from the methanol fraction under reduced pressure. The residue was partitioned between water (200 ml) and ethyl acetate (3×200 ml) and the aqueous phase discarded. The ethyl acetate phase was filtered through a small plug of silica gel and the solvent evaporated to give 22.4 g of neem extract.

The neem extract was stirred overnight in 225 ml methanol with activated carbon (5 g) and the carbon was removed by filtration.

The methanol solution was hydrogenated over 10% palladium on carbon (Pd/C) at 40 lb/in$^2$ (psi) of hydrogen until no more azadirachtin could be detected by HPLC. The solution was then filtered and evaporated to give 15.7 g of the hydrogenated final product.

Analysis by HPLC (65:35 MeOH/H$_2$O; 1 ml/min, 3u C-18) indicated that the residue contained 25% dihydroazadirachtin.

EXAMPLE 2

Ground neem kernels (10 kg) and 20 liters of heptane were stirred for 1 hour. The liquid phase was separated and the procedure repeated using 10 liters of heptane.

After the second heptane wash, the cake was stirred three times for 1 hour each with 10 liters of 95% methanol. The combined washings consisted of the upper heptane phase, (4 liters) and the lower methanol phase (15 liters). The methanol phase was separated and its volume reduced to 4 liters by distillation at atmospheric pressure.

Water (3 liters) and then 1 kg of active charcoal were added and the mixture was stirred overnight.

After Buchner filtration through a paper filter, the volume of the liquid phase was reduced in vacuo at 40° C. to about 3 liters. About 1 liter of brine was added and the mixture was extracted continuously with heptane overnight.

The azadirachtin mixture was then extracted from the aqueous phase with ethyl acetate:heptane (9:1) using 3×0.5 liters of the solvent mixture. After separation, the organic layer was diluted with additional 0.5 liters of heptane and washed with brine (3×1 liter). The organic layer was dried over magnesium sulfate and stripped of the solvents to leave pale-yellow powdery residue.

The residue was analyzed by HPLC (65:35 MeOH/H$_2$O; 1 ml/min; 3u C-18). The results are detected simultaneously by uv (211 nm) and refractive index. In FIG. 1, curve A shows the uv result and curve B shows the refractive index. Peak X corresponds to azadirachtin and Peak Y corresponds to tigloylazadirachtol. Other known compounds in the residue include salinin (Peak M), nimbin (Peak N), and 3-acetoxy-7-tigloyl-vilasinin lactone(Q). By comparison with a sample of the pure compound in solution of known concentration, it was calculated that the residue contained about 25% by weight azadirachtin.

To a solution of 25.0 grams of the residue in 250 ml of methanol, there was added 0.5 grams of 10% Pd/C and the mixture was hydrogenated under 40 psi of hydrogen overnight. The mixture was filtered and the solvent was removed in vacuo to yield 17.6 grams of powdery residue.

Figure 2:
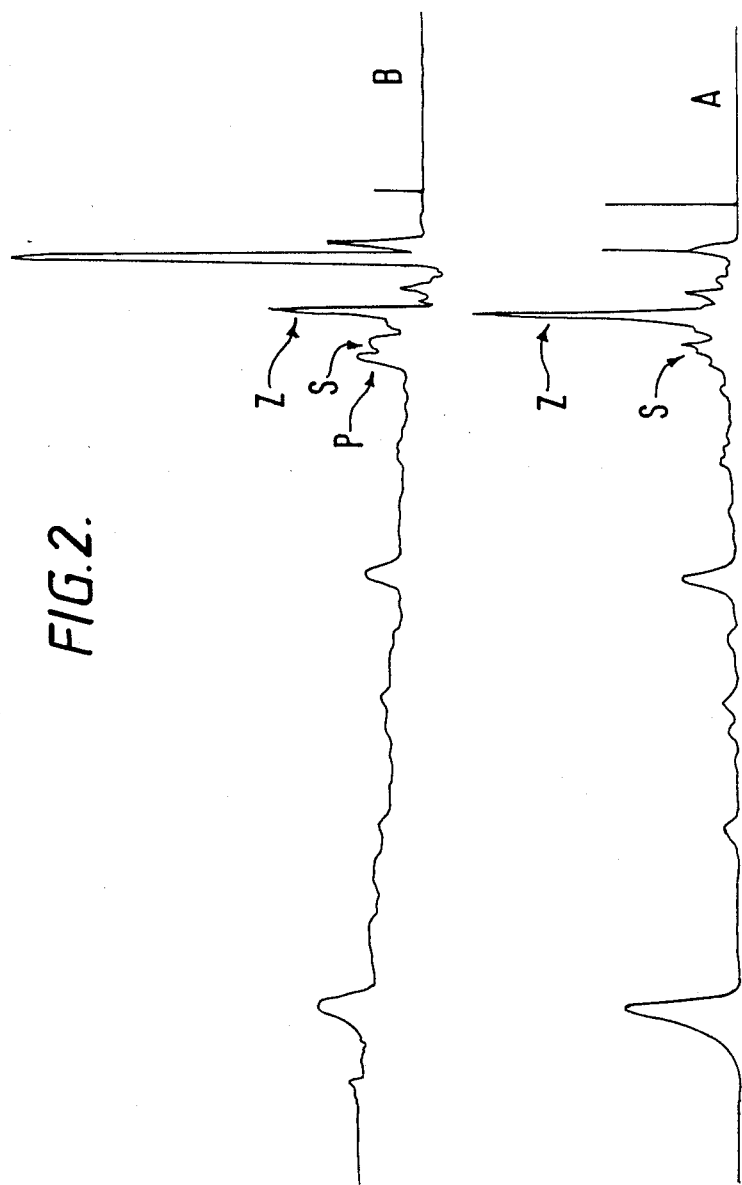
FIG. 2 shows the uv absorption (A) and refractive index (B) for a hydrogenated neem seed extract of the invention.

The residue was analyzed by HPLC. FIG. 2 shows the HPLC uv curve (A) and the refractive index, Rl, (B) for the residue.

By comparison with a sample of the pure compound of known concentration it was calculated that the residue contained about 25% dihydroazadirachtin.

Peak Z corresponds to dihydroazadirachtin. The HPLC of this insecticidal hydrogenated extract of the invention is also characterized by Peak S and by a peak which appears in the refractive index Curve B and not in the uv curve, Peak P.

EXAMPLE 3

A mixture of 100 g of ground neem kernels, 255 ml of methanol and 14 ml of water was stirred at room temperature for 45 minutes and then filtered. The filter cake was washed with 538 ml of 95% methanol over a half hour period. The combined methanol washings were extracted with heptane (3×200 ml) and the solvent was removed from the methanol layer under reduced pressure.

The residue is partitioned between water and ethylacetate essentially as described in Example 1 to yield about 600 mg of extract.

EXAMPLE 4

The neem extract was hydrogenated using nickel boride as catalyst using the following procedure.

Three solutions were prepared as follows

Solution A: Nickel acetate tetrahydrate (Ni(OAC)$_4$.4H$_2$O, 15 g) was dissolved in 33 ml of water. Stirring and gentle heating below 100° C. was applied to facilitate the dissolution of the salt.

Solution B: Neem seed extract (90 g) containing 30–50% azadirachtin was dissolved in 450 ml of absolute methanol at room temperature.

Solution C: To 4.84 g of sodium borohydride powder (NaBH$_4$, 98%, Aldrich), 60 ml of water was added in one portion with stirring. Since this solution decomposes slowly with the evolution of hydrogen, it was used immmediately after it was prepared.

Solutions A and B were mixed in a 1 liter reaction flask equipped with a mechanical stirrer. Under a nitrogen atmosphere, Solution C was added via an addition funnel over 5 minutes with ice bath cooling. The mixture was stirred for an additional 5 minutes and then transferred into a 2 liter Parr flask and hydrogenated at room temperature under 55 psi of hydrogen. The progress of the hydrogenation was monitored by HPLC on a C-18 reverse phase column (Zorbax ODS (DuPont), 4.6 mm×25 cm) at 1.5 ml/min., using 3:7 water/methanol as the mobile phase.

After the hydrogenation was complete (complete conversion of Peak X into Peak Z, FIGS. 1 and 2), the nickel boride catalyst was removed by centrifuging the reaction mixture and decanting the clear supernatant.

The solvent was removed in vacuo and the residue was triturated with 100 ml water. The water phase was filtered off and extracted with EtOAc (3×50 ml). The organic fractions were combined, dried over MgSO$_4$ (10 g), filtered and the solvent was removed in vacuo at 30° C. to yield hydrogenated extract.

Alternatively, the mixture of Solution A and Solution B was added under nitrogen, with stirring and cooling to Solution C.

EXAMPLE 5

The neem seed extract was hydrogenated in various solvents using Raney nickel to catalyze the reaction. The neem extract (1.0 g) containing 25–50% of azadirachtin was dissolved in 50 ml of solvent and 1.5 ml of wet Raney nickel was added to the solution. The reaction mixture hydrogenated under 55 psi of hydrogen in a Parr hydrogenator overnight.

The mixture was then analyzed by HPLC to determine the percent conversion of azadirachtin to dihydroazadirachtin. The results are shown in following Table I.

TABLE I

| Solvent | Percent Conversion |
| --- | --- |
| 1. 6:3:1, ethyl acetate:water:methanol | 100 |
| 2. 7:3, ethyl acetate:water | 100 |
| 3. 100% ethyl acetate | 100 |
| 4. 95% aqueous methanol | 100 |

Compositions and formulations according to the present invention may also include known pesticidal compounds. This expands the spectrum of activity of the preparations and may give rise to synergism.

The following known insecticidal, fungicidal and acaricidal compounds are non-limiting examples of compounds used in such a combined preparation.

Insecticides such as:

Chlorinated hydrocarbons, for example, 2,2-bis(p-chlorophenyl)-1,1,1-trichloroethane and hexachloroepoxyoctahydrodimethanonaphthalene;

Carbamates, for example, N-methyl-1-naphthylcarbamates;

Dinitrophenols, for example, 2-methyl-4,6-dinitrophenol and 2-(2-butyl)-4,6-dinitrophenyl-3,3-dimethylacrylate;

Organic phosphorus compounds, such as dimethyl-2-methoxy-3-carbonyl-1-methylvinyl phosphate, 0,0-diethyl-O-p-nitrophenylphosphorothioate; N-monomethylamide of 0,0-dimethyldithiophosphorylacetic acid;

Diphenylsulfides, for example, p-chlorobenzyl or p-chlorophenyl sulfide and 2,4,4', 5-tetrachlorodiphenyl-sulfide;

Diphenylsulfonates, for example, p-chlorophenylbenzenesulfonate;

Methylcarbinols, for example, 4,4-dichloro-1-trichloromethylbenzhydrol;

Quinoxaline compounds, such as methylquinoxaline dithio-carbonate;

Amidines such as N'-(4-chloro-2-methylphenyl) N,N-dimethylformamidine;

Pyrethroids such as Allethrin;

Biologicals such as *Bacillus thuringiensis* preparations;

Organic tin compounds such as tricyclohexyltin hydroxide;

Piperonyl butoxide.

Fungicides such as:

Organic mercury compounds, for example, phenylmercuryacetate and methylmercurycyanoguanide;

Organic tin compounds, for example, triphenyltin hydroxide and triphenyltin acetate;

Alkylenebisdithiocarbamates, for example, zinc ethylene-bisdithiocarbamate and manganese ethylenebisdithiocarbamate; and 2,4-dinitro-6-(2-octyl-phenylcrotonate,), 1-bis(dimethylamino)-phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetra-hydrophthalimide, N-dichlorofluoromethylthio-N-phenyl-N'-dimethylsulfonyldiamide and tetrachloroiso-phthalonitrile.

It has been found by biological evaluation that hydrogenated neem seed extracts according to the present invention have pesticidal activity and are capable of controlling larvae and adult forms of pests. It has also been found that the hydrogenated material of the invention has improved residual activity when compared to non-hydrogenated neem seed extract. One skilled in the art will know how to determine the activity of a given hydrogenated extract against a given insect and the dosage required.

In evaluating the pesticidal activity of the extracts of this invention, the following test procedures were employed.

Circular leaf discs 3 cm in diameter were punched out of the first true leaves of lima bean (*Phaseolus limensis* var. Woods' Prolific) and their upper surface was painted with 35 ul/disc of test emulsion containing the extract, 5% methanol, 5% acetone, 0.1% blend of alkylaryl polyethoxyethoxylate and sodium salt of alkylsulfonated alkylate (Triton ® CS-7 surfactant from Rohm and Haas Co., Philadelphia, PA) and 89.9% water. The check discs received blank emulsion containing all ingredients with the exception of the test extract. The treated discs were individually placed in Gelman petri dishes (5 cm diameter) containing a 4.7 cm diameter moist Gelman filter pad (1.5 ml water per pad).

After the emulsion evaporated to dryness, the leaf discs were infested with third instar larvae of Southern armyworm, *Spodoptera eridania* (one insect per dish). The dishes were then covered. All treatments were repeated five times. The percent feeding and percent mortality were determined visually 6 days after treatment.

To eliminate the error due to mortality factors unrelated to antifeeding activity, tests in which not all larval survived the first 48 hours were routinely repeated.

The results obtained for hydrogenated extract and non-hydrogenated extract at 1000, 333 and 167 ppm of extract (approximately 250, 80 and 40 ppm of azadirachtin or dihydroazadirachtin) are listed in Table II.

TABLE II

| Compound | ppm extract | ppm ai* | % feeding control | % kill |
| --- | --- | --- | --- | --- |
| $H_2$-neem seed extract | 1000 | 242 | 97 | 80 |
|  | 333 | 81 | 95 | 80 |
| neem seed extract | 1000 | 250 | 94 | 40 |
|  | 333 | 83 | 86 | 20 |
|  | 167 | 41 | 74 | 20 |

*a = dihydroazadirachtin or azadirachtin concentration (determined by HPLC)
% feeding control = 100 × (1 − % feeding/% feeding by stock)

In evaluating the 7-day residual activity of the extracts of this invention, the following test procedures were employed.

A test solution containing 150 parts per million (ppm of azadirachtin or dihydroazadirachtin was made by dissolving the test extract in a solvent (acetone: methanol, 1:1 v/v), adding a surfactant and then water to give an acetone: methanol water system of 10:10:80. A 1:1 mixture of an alkylarylpolyether-alcohol (Triton ® X-155 surfactant from Rohm and Haas Co., Philadelphia, PA) and a modified phthalic glycerol alkyl resin (Triton ® B-1956 surfactant from Rohm and Haas Co., Philadelphia, PA) was used at the equivalent of 1 ounce per 100 gal. of test solution as a surfactant. Analogous solutions were made by serially diluting the 150 ppm test solution with water and surfactant to give concentrations of 38 and 10 ppm.

Evaluations were made on the following pests:

| Code Symbol | Common Name | Latin Name |
| --- | --- | --- |
| SAW | Southern Armyworm | *Spodoptera eridania* |
| MBB | Mexican Bean Beetle | *Epilachna Varivestis* |
| TBW | Tobacco Budworm | *Heliothis Virenscens* |

For the Mexican Bean Beetle and Southern Armyworm test, lima bean (*Phaseolus limensis* Var. Woods' Prolific) plants 2-3 weeks old were sprayed to run off with the test solution. After seven days, the treated leaves were detached and artificially infested with the target pests (3rd instar larvae - 5 insects/treatment). The percent insect control was determined 6 days after infestation.

For the Tobacco Budworm test, cotton (*Gossypium hirsutum*) plant 2-3 weeks old were sprayed to run off with the test solution. After seven days, the treated leaves were detached and artificially infested with 1st instar larvae of tobacco budworm (5 insects/treatment). The percent insect control was determined 6 days after infestation.

The results are listed in Table III.

TABLE III

| | | 7-Day Residual Test | | |
| --- | --- | --- | --- | --- |
| Compound | Crop | Pest | 10 ppm | 38 ppm | 150 ppm |
| H$_2$-neem seed extract | Bean | SAW | 20 | 20 | 40 |
| neem seed extract | Bean | SAW | 0 | 0 | 40 |
| H$_2$-neem seed extract | Cotton | TBW | 100 | 100 | 100 |
| neem seed extract | Cotton | TBW | 60 | 60 | 100 |
| H$_2$neem seed extract | Bean | MBB | 50 | 80 | 100 |
| neem seed extract | Bean | MBB | 40 | 40 | 80 |

It should be understood that the instant specification and examples are set forth by way of illustration and not limitation and that various modifications and changes may be made without departing from the spirit and scope of the present invention as defined by the appended claims.

I claim:

1. Hydrogenated crude extract of seeds of the neem tree *Azadirachta indica*.

2. Hydrogenated crude extract of seeds of the neem tree *Azadirachta indica* which is obtained by hydrogenating an insecticidal extract of the seeds.

3. The hydrogenated extract of claim 1 containing dihydroazadirachtin.

4. The hydrogenated extract of claim 3 which contains from about 5% to about 80% dihydroazadirachtin.

5. The hydrogenated extract of claim 4 which contains from about 15% to about 50% dihydroazadirachtin.

6. An insecticidal composition which comprises an agronomically acceptable carrier and an insecticidally effective amount of the extract of claim 2.

7. An insecticidal crude extract of neem seed containing azadirachtin which is hydrogenated until substantially all of the azadirachtin in the extract has been converted to dihydroazadirachtin or tetrahydroazadirachtin.

8. An insecticidal hydrogenated crude neem seed extract produced by extracting seeds of the neem tree with a polar solvent to obtain an extract and hydrogenating said extract.

9. The insecticidal extract of claim 8 wherein the extraction comprises the steps of grinding the neem seeds into particles from about 0.1 to about 10 mm in diameter and extracting the ground seeds with a polar solvent to obtain the neem seed extract.

10. The insecticidal extract of claim 8 wherein the extraction further comprises the step of removing fatty acids and oils by extracting with a non-polar solvent.

11. The insecticidal extract of claim 10 wherein the fatty acids and oils are removed from the ground neem seeds prior to extracting the neem seeds with a polar solvent.

12. The insecticidal extract of claim 10 wherein the extract obtained from the polar solvent extract of the neem seeds is treated with a non-polar solvent to remove fatty acids and oils.

13. The insecticidal extract of claim 9 wherein the polar solvent is methanol or ethanol.

14. The insecticidal extract of claim 10 wherein the non-polar solvent is hexane or heptane.

15. The insecticidal extract of claim 8 wherein the hydrogenation is carried out under pressure in the presence of a catalyst.

16. The insecticidal extract of claim 15 wherein the catalyst is palladium on carbon or platinum oxide.

17. The insecticidal extract of claim 15 wherein the catalyst is nickel boride or Raney nickel.

18. The insecticidal extract of claim 15 wherein the hydrogenation is carried out at from about 1 to about 60 atmospheres of hydrogen at from about 10° C. to about 50° C.

19. The insecticidal extract of claim 17 wherein the hydrogenation is carried out at from about 2 to about 4 atmospheres of hydrogen at about 20° C.

20. An insecticidal hydrogenated crude neem seed extract produced by grinding neem seed to a particle size of from about 0.1 to about 10 mm in particle diameter, extracting the particles with a polar solvent to obtain a neem seed extract, and hydrogenating the neem seed extract at from about 1 to about 60 atmospheres of hydrogen at from about 10° C. to about 50° C.

21. A method of controlling insects which comprises contacting the foliage with an insecticidally effective amount of the compound of claim 2.

22. The method of claim 20 wherein the extract is applied at from about 0.1 grams to about 10 kilograms per hectare.

23. The method of claim 20 wherein the extract is applied at from about 5 grams to about 200 grams per hectare.

24. An insecticidal composition which comprises an agronomically acceptable carrier and an insecticidally effective amount of the extract of claim 7.

25. A method of controlling insects which comprises contacting the foliage with an insecticidally effective amount of the hydrogenated extract of claim 7.

26. An insecticidal composition which comprises an agronomically acceptable carrier and an insecticidally effective amount of the hydrogenated extract of claim 8.

27. A method of controlling insects which comprises contacting the foliage with an insecticidally effective amount of the hydrogenated extract of claim 8.

28. Hydrogenated crude extract of the neem tree *Azadirachta indica* which is obtained by hydrogenating an azadirachtin-containing extract of the neem tree.

29. Hydrogenated crude extract from a plant which is obtained by hydrogenating an azadirachtin-containing extract from a plant.

* * * * *